(12) United States Patent
Albee et al.

(10) Patent No.: US 10,389,202 B2
(45) Date of Patent: Aug. 20, 2019

(54) CONTAMINANT-RESISTANT MOTORS FOR SURGICAL INSTRUMENTS

(71) Applicant: AMERICAN PRECISION INDUSTRIES, INC., West Chester, PA (US)

(72) Inventors: William A. Albee, West Chester, PA (US); Andrew R. Sharp, Ardmore, PA (US); Jerry Vitale, West Chester, PA (US)

(73) Assignee: American Precision Industries, Inc., West Chester, PA (US)

( * ) Notice: Subject to any disclaimer, the term of this patent is extended or adjusted under 35 U.S.C. 154(b) by 129 days.

(21) Appl. No.: 15/466,762

(22) Filed: Mar. 22, 2017

(65) Prior Publication Data

US 2017/0279328 A1 Sep. 28, 2017

Related U.S. Application Data

(60) Provisional application No. 62/311,521, filed on Mar. 22, 2016.

(51) Int. Cl.
| | |
|---|---|
| *H02K 5/12* | (2006.01) |
| *H02K 5/10* | (2006.01) |
| *A61B 90/70* | (2016.01) |
| *A61B 17/32* | (2006.01) |
| *A61B 90/00* | (2016.01) |

(52) U.S. Cl.
CPC .......... *H02K 5/10* (2013.01); *A61B 17/32002* (2013.01); *A61B 90/70* (2016.02); *A61B 2090/0813* (2016.02)

(58) Field of Classification Search
CPC .................................. H02K 5/10; H02K 5/00
USPC ............................................. 310/88, 89, 68 B
See application file for complete search history.

(56) References Cited

U.S. PATENT DOCUMENTS

| | | | | |
|---|---|---|---|---|
| 5,233,248 | A * | 8/1993 | Kawamura | ............ H02K 1/185 310/156.25 |
| 5,291,087 | A * | 3/1994 | Pollick | .................. F04D 23/008 310/86 |
| 5,565,721 | A * | 10/1996 | Knappe | ................... G01P 3/487 310/156.22 |
| 2010/0327537 | A1 * | 12/2010 | Johnson | ................. H02K 5/128 277/405 |

(Continued)

*Primary Examiner* — Hanh N Nguyen
(74) *Attorney, Agent, or Firm* — Reising Ethington P.C.

(57) ABSTRACT

A contaminant-resistant motor may include an endbell with hermetic sealing of control components within a control module cavity in the endbell. The endbell configuration includes a front wall that isolates the control module cavity from contaminant-prone area of the motor assembly. The stator leads may be sealed within the lead passages using glass or other seals to further isolate the stator leads and control module cavity against ingress of contaminating liquids from the motor interior. The endbell configuration permits larger bearing elements to be used. A method of assembly of the motor may involve first fixture to align the stator, housing and REB to ensure concentric alignment of the stator to housing and the REB to the housing and a second fixture to isolate front and rear bearing bores and the stator inner diameter from encapsulation material and permit the stator to be molded to the housing.

20 Claims, 6 Drawing Sheets

(56) References Cited

U.S. PATENT DOCUMENTS

| | | | | |
|---|---|---|---|---|
| 2011/0120073 A1* | 5/2011 | Flanary | ............. | H02K 5/08 |
| | | | | 56/250 |
| 2014/0294625 A1* | 10/2014 | Tucker | ............. | H02K 5/12 |
| | | | | 417/410.1 |
| 2015/0300841 A1* | 10/2015 | Campbell | ............ | G01D 5/20 |
| | | | | 417/410.1 |

* cited by examiner

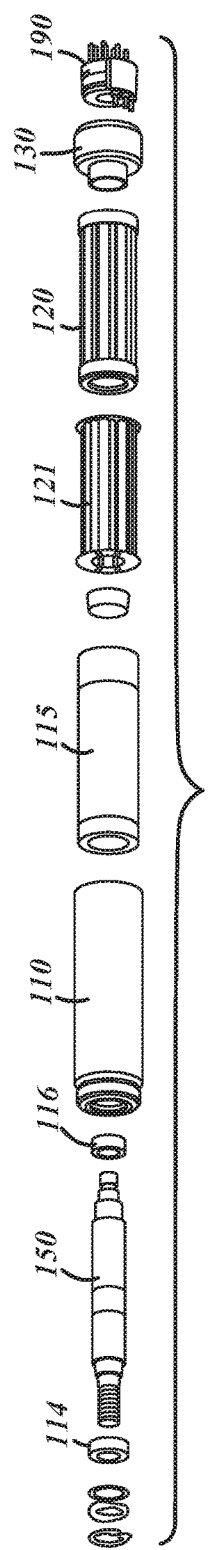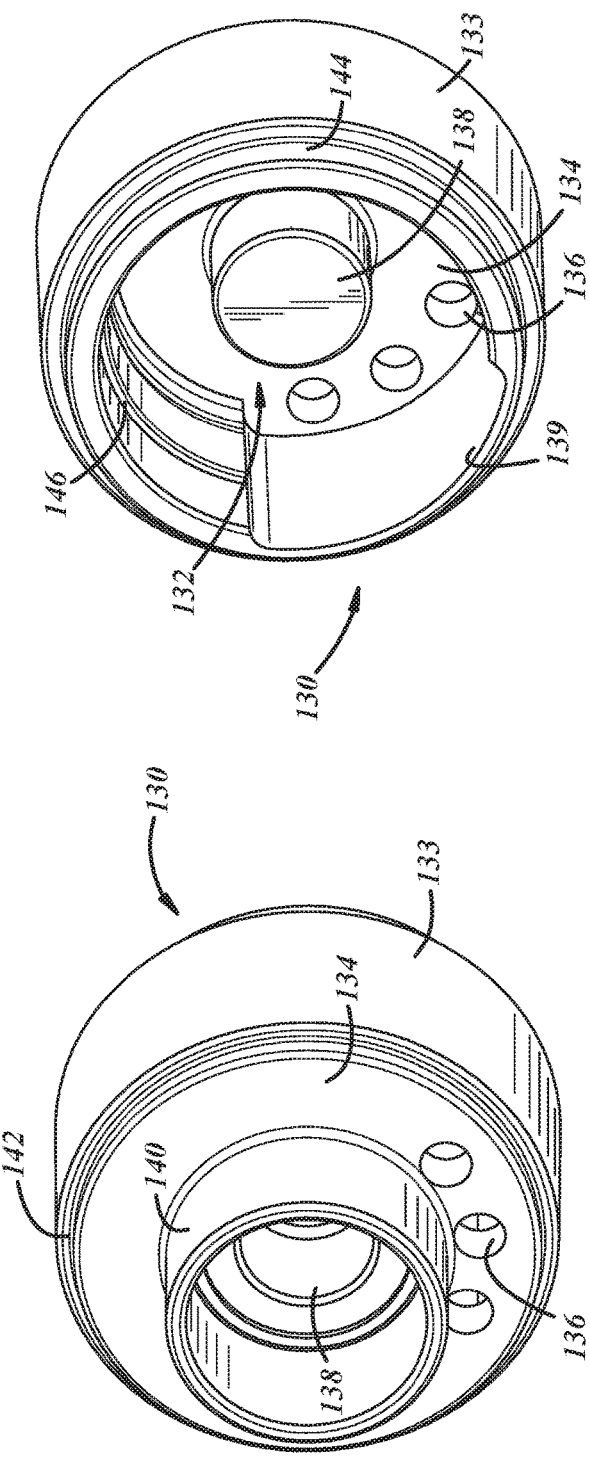

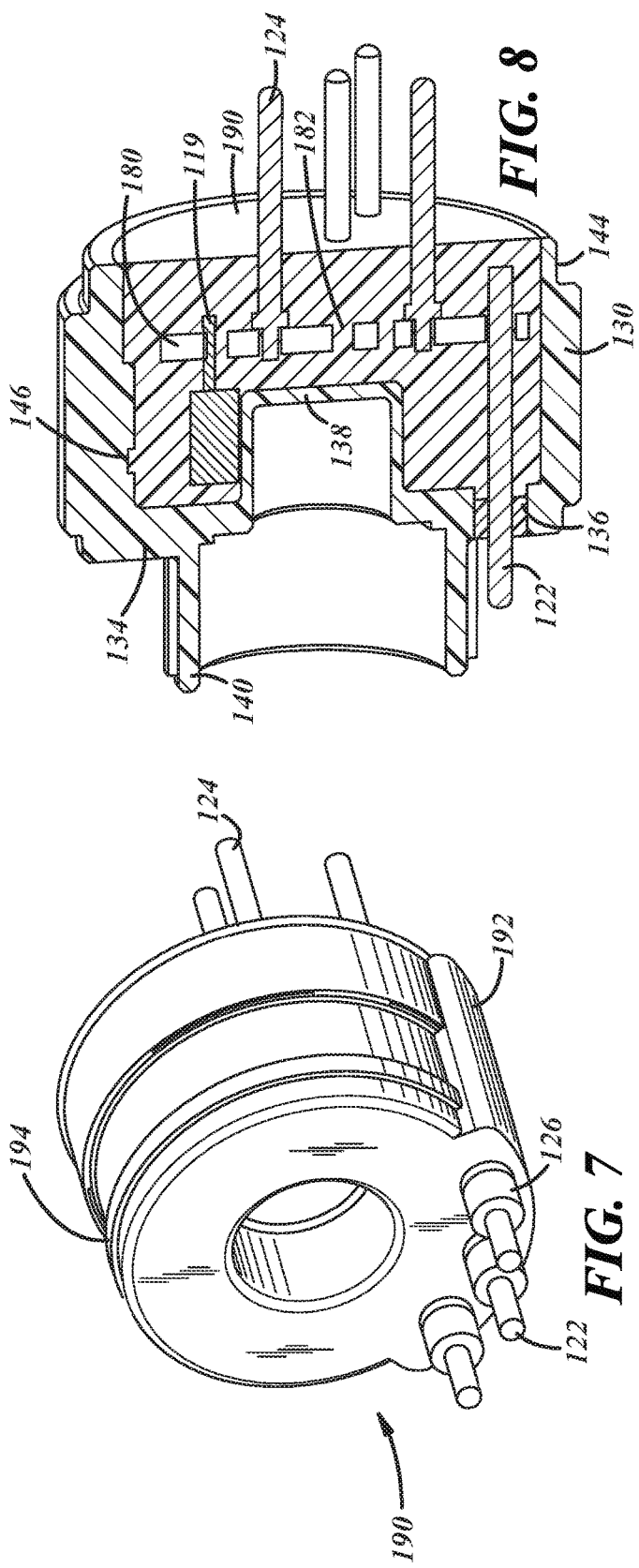
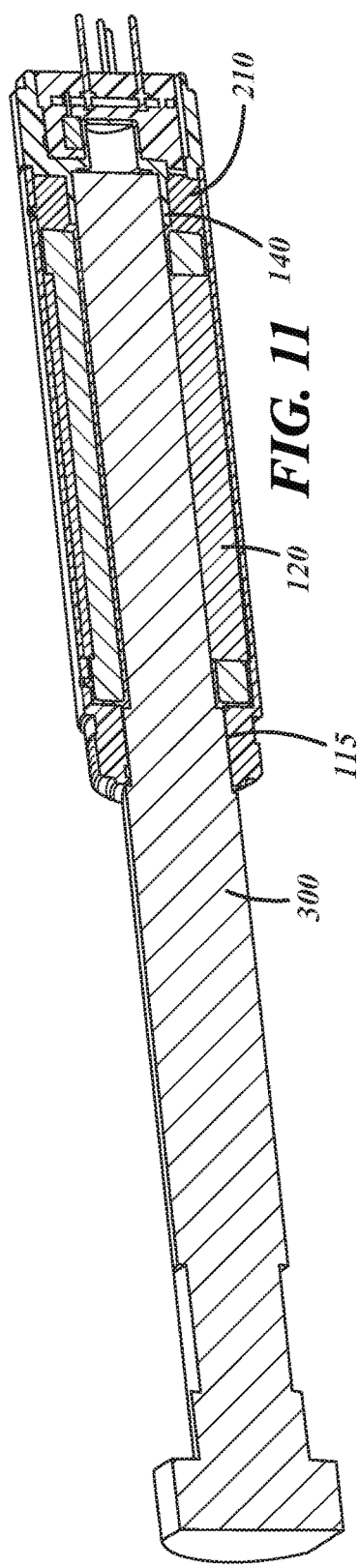

CONTAMINANT-RESISTANT MOTORS FOR SURGICAL INSTRUMENTS

CROSS-REFERENCE TO RELATED APPLICATIONS

The instant application claims the benefit under all applicable laws, treaties, conventions and regulations, of U.S. Provisional Application No. 62/311,521 titled METHOD AND SYSTEM FOR IMPROVED SURGICAL INSTRUMENT, filed on Mar. 22, 2016. The subject matter described in that application is incorporated herein by reference in its entirety. Where an element or subject matter of the aforementioned provisional application or a part of the description, claims or drawings in the aforementioned provisional application is not otherwise contained in this application, that element, subject matter or part is incorporated by reference in this application for the purposes of any and all applicable rules, procedures or laws.

FIELD

The disclosure relates to electric motors and for use in devices that may be exposed to harsh environments, such as medical devices and surgical instruments that may be exposed to sterilization and harsh operating environments. More particularly, the disclosure relates to electric motor structures having decreased environmental sensitivity and increased resistance to contamination, leakage and wear when exposed to harsh environments.

BACKGROUND

There are a number of factors influencing the development of economical and dependable state-of-the-art medical devices and surgical instruments, and the electromechanical systems, controls and sensors that may be incorporated into such devices. One factor is the healthcare cost savings that result from the use of reusable instruments instead of single use, disposable instruments or components which may be discarded as infectious waste. Another factor is the desirability of extending the ergonomic range provided by such devices to achieve a high degree of utility by both male and female surgeons. Yet another factor is the ever-increasing desire to demonstrate favorable patient outcomes while also demonstrating cost-effectiveness, especially in cases where access to cutting-edge surgical procedures and surgeons, real-time visualization of procedures, and precision have a clinical premium. Yet another factor is continued improvement in the automation and control provided by surgical instruments and empowering surgeons of a given skill level to consistently achieve excellent patient outcomes. Still another factor is the ever-increasing demand worldwide for affordable and modern healthcare solutions. All of these factors result in a desirability for reusable surgical instruments that continue to operate dependably after multiple exposure to cleaning, sterilization and operating environments.

Generally, it is desirable to decrease the environmental sensitivity of such surgical instruments and the electromechanical components, sensors, electronics and power sources upon which they rely. In order for an instrument to be reused following a given surgical procedure, it must be cleaned or washed, sterilized, and possibly recharged prior to reuse on another patient. Cleaning or washing may involve the removal of gross biological debris accumulated during a previous use. All blood, bodily fluids, tissue and any single use components may require removal or disassembly and cleaning with wipes, brushes, and/or enzyme-based detergents. Some single-use components, such as staple cartridges, may be utilized in reusable devices and require removal and disposal, as well as replenishment.

Cleaning and washing may involve exposing the surgical instrument to a special purpose washer, such as a dishwasher, which utilizes high temperature, high pH, aqueous detergents to automatically wash, neutralize and rinse the device. Neutralization may involve the use of a low pH solution (pH 2.6-3). After rinsing, the device is typically sterilized as a final step prior to surgical reuse. Sterilization is primarily achieved through steam in an autoclave. There are alternate methods for achieving sterilization as a final step, but steam sterilization is most common. Autoclaves are a preferred method of the medical industry for sterilizing surgical instruments and medical devices, including implants. Autoclaves involve variations of pressure and temperature in a sealed environment.

Surgical instruments may be exposed to other sterilization environments. For example, ETO (ethylene oxide), peroxide and wet-sterilization soaks, such as those sold under the name CIDEX®, may be utilized. Radiation may also be used in such procedures. Thus, reusable surgical instruments must be robust and resistant to degradation and contamination that may result from repeated exposure to such environments.

Medical devices and surgical instruments often incorporate electric motors for providing electromotive power to such devices. For example, a shaver designed for arthroscopic applications may employ a miniature electric motor for driving a shaving blade to precisely remove soft tissue in an arthroscopic surgical procedure. Such instruments, and therefore the motors that power them, may be exposed harsh environments in washing and sterilization processes as well as in the devices surgical operating environment itself.

The operating environment for a surgical device may present additional environmental challenges. For example, shavers that are used to trim and remove biological tissue may be operated in an arthroscopic surgical field, where the surgical field is viewed during the procedure with an endoscope, and a surgical space is created using pressurized surgical solution to which the instrument is exposed. The pressurized surgical solution may itself foster a harsh environment for the operation of the surgical instrument.

Operation of surgical instruments in environments that involve surgical solutions may add additional challenges that need to be addressed in the design of the instrument and in any electric motor or electromotive power component that may be integrated into the instrument. Such components may be exposed to a pressurized, aqueous and corrosive environment. Furthermore, the surgical solution may also be electrically conductive. Therefore, such components must be resistant to corrosion, resistant to ingress of pressurized fluid, and must electrically isolate the electronics and control components from the external environment. The high-iron alloys that may be typically used in magnetic circuits or other motor or control components may be particularly susceptible to corrosion, as are hardenable alloys, typically used in many long-life, rolling element bearing (REB) structures, such as 400 series allows. Still further, neodymium iron magnets that may be utilized in electric motors, may be susceptible to corrosion from surgical solutions. Such surgical solutions may also degrade the insulating properties of polymers used in surgical instruments as well as the lubricants and bearings used in motors and other components in the surgical instrument. The repeated use of reusable surgical components in surgical solution, cleaning and sterilization environments further compounds the detrimental effects of such environments on the integrity of a surgical device and electric motor components incorporated therein.

With particular regard to electric motors utilized in many surgical instruments, there are two areas where the harsh operating and sterilization environments may result in particularly detrimental effects on the motor components and thus motor operation and dependability. First, the motor may be more prone to bearing degradation or failure due to loss of lubricant (grease), corrosion and wear. Second, motor sensors, which may typically be Hall effect sensors in a brushless motor configuration, may be prone to degradation or failure due to moisture and ingress of surgical solution or other contaminants within the motor interior.

FIG. 1 illustrates a prior art electric motor configuration that may be used in a shaver surgical instrument, for example. The housing assembly 10 houses commutation magnets 12, front and rear ball bearings, 14 and 16, hall sensors 18 and stator 20. A printed circuit board (PCB) 21 may support electronic components, which among other functions, may provide control of current to the stator, based on information or analog signals from hall sensors 18. At least one stator to printed circuit board (PCB) lead connection 22 extends from the PCB to the stator. External leads 24 for power and control connections extend from the housing assembly 10. The PCB and hall sensors 18, as well as other components may be housed within a rear endbell 30. Such prior art configurations may be prone to ingress of surgical solution along the path "P" shown in FIG. 1, where deterioration of the seals may permit ingress from outside the housing assembly, across front bearing 14, along a space between the stator and rotor and to a space within the housing assembly where the stator to PCB lead connection 22 is exposed to the housing interior. Ingress of surgical solution or external contaminants may also occur along the space between the stator elements 20 and the housing wall, as well as through the endbell 30 and into an encapsulation compound used in sealing of the components within the rear endbell 30.

Thus, electric motor configurations of the prior art suffer from a number of disadvantages in being able to provide for continued reuse without contamination or other detrimental effects that result from exposure to harsh environments. It would therefore be desirable to provide electric motor structures for surgical instruments that address the aforementioned disadvantages and shortcomings and others.

SUMMARY

According to one aspect of the disclosure, a contaminant-resistant motor may include an endbell with a configuration that provides for hermetically sealing of control components within a control module cavity defined in the endbell. The endbell configuration includes a front wall that isolates the control module cavity from contaminant-prone area of the motor assembly. The configuration provides a number of sealing features for facilitating secure and isolated encapsulation of control components in the control module cavity. A number of stator lead passages are positioned in a recessed area of the end bell for ease of assembly and maximized encapsulation of the stator leads. The stator leads may be sealed within the lead passages using glass or other seals to further isolate the stator leads and control module cavity against ingress of contaminating liquids from the motor interior.

According to another aspect, durability of motor bearings is enhanced by the use of larger bearing elements, which is made possible by the endbell configuration. Sensors may be positioned behind the bearing element in the rear endbell, providing a larger space to accommodate the bearing. The larger bearing structure, combined with improved bearing construction and lubricants, may provide improved bearing life.

According to another aspect, components of the motor assembly, including stator elements, are assembled using fixtures. A first fixture may include an alignment pin to be used to align the stator, housing bearing bore and rear end bell bearing bore to ensure concentric alignment of these components. A second fixture may include a pin to be used to isolate the front and rear bearing bores and the stator inner diameter from encapsulation material to prevent encapsulant from entering these areas when encapsulant is introduced to an area on the motor side of the rear end bell during an encapsulation step.

Unless otherwise defined, all technical and scientific terms used herein have the same meaning as commonly understood by one of ordinary skill in the art to which the described invention pertains. Although other implementations, methods and materials similar to those described herein can be used to practice the invention, suitable and example implementations, methods and materials are described below. All publications, patent applications, and other references mentioned herein are incorporated by reference in their entirety. In case of conflict, the present specification, including definitions, will control. In addition, the materials, methods and examples are illustrative only and are not intended to be limiting in any way. The details of one or more example implementations of the invention are set forth in the accompanying drawings and the description below. Other features, objects and advantages of the invention will be apparent from the description and drawings, and from the claims.

DESCRIPTION OF THE DRAWINGS

The above and other attendant advantages and features of the invention will be apparent from the following detailed description together with the accompanying drawings, in which like reference numerals represent like elements throughout. It will be understood that the description and embodiments are intended as illustrative examples and are not intended to be limiting to the scope of invention, which is set forth in the claims appended hereto.

FIG. 4 is an exploded perspective view of an example motor configuration according to an aspect of the disclosure.

FIG. 5 is detailed front perspective view of an example motor rear endbell according to an aspect of the disclosure.

FIG. 6 is a detailed rear perspective view of an example motor rear endbell according to an aspect of the disclosure.

FIG. 7 is detailed front perspective view of an example endbell control module cavity encapsulation according to an aspect of the disclosure.

FIG. 8 is a sectional view of an example endbell and encapsulation according to an aspect of the disclosure.

FIG. 11 is a cross-section of an example pin used in a motor assembly process according to an aspect of the disclosure.

DETAILED DESCRIPTION

Figure 1:
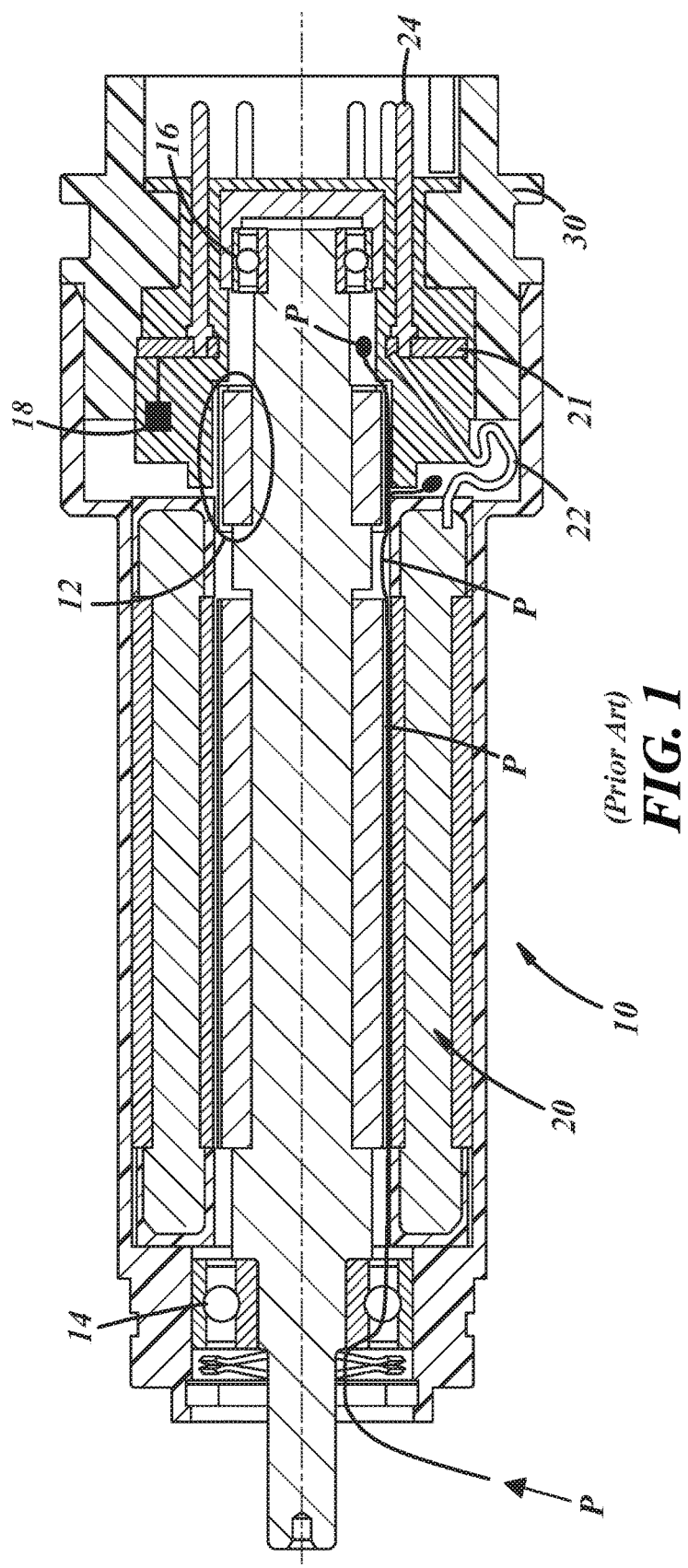
FIG. 1 is cross-section of a prior art motor configuration as discussed above.
Figure 2:
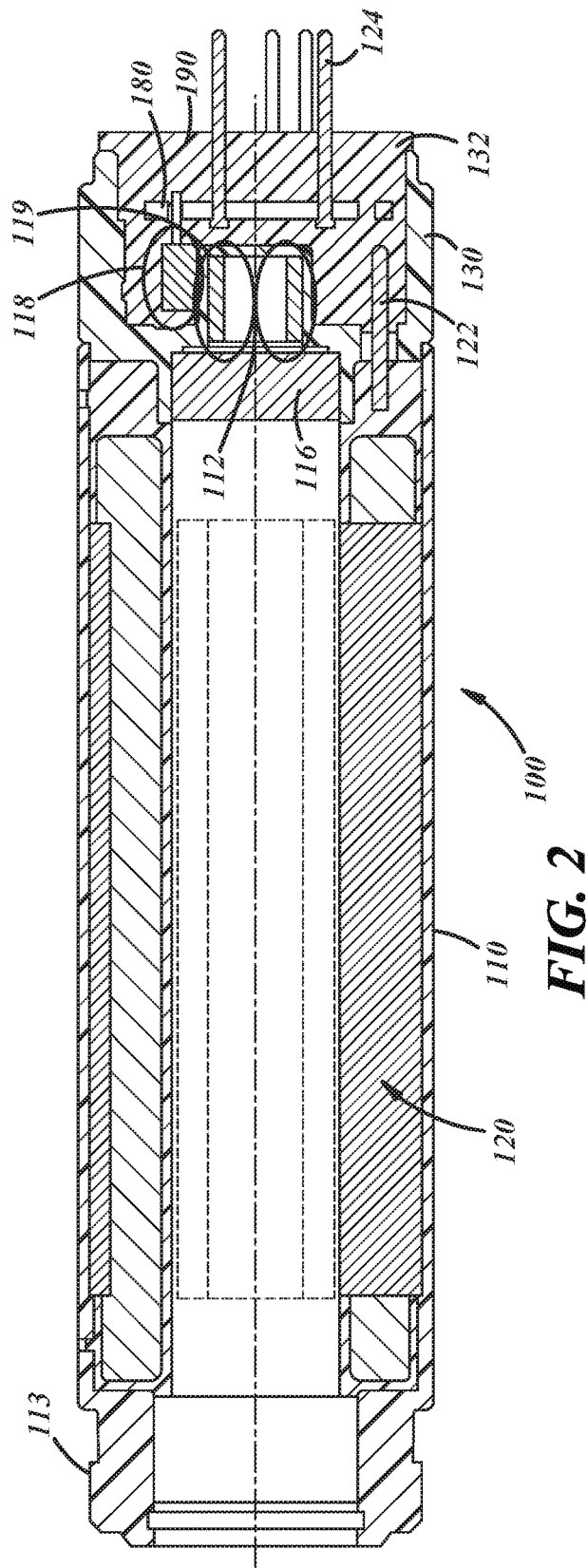
FIG. 2 is a cross-section of an example motor configuration according to an aspect of the disclosure.
Figure 3:
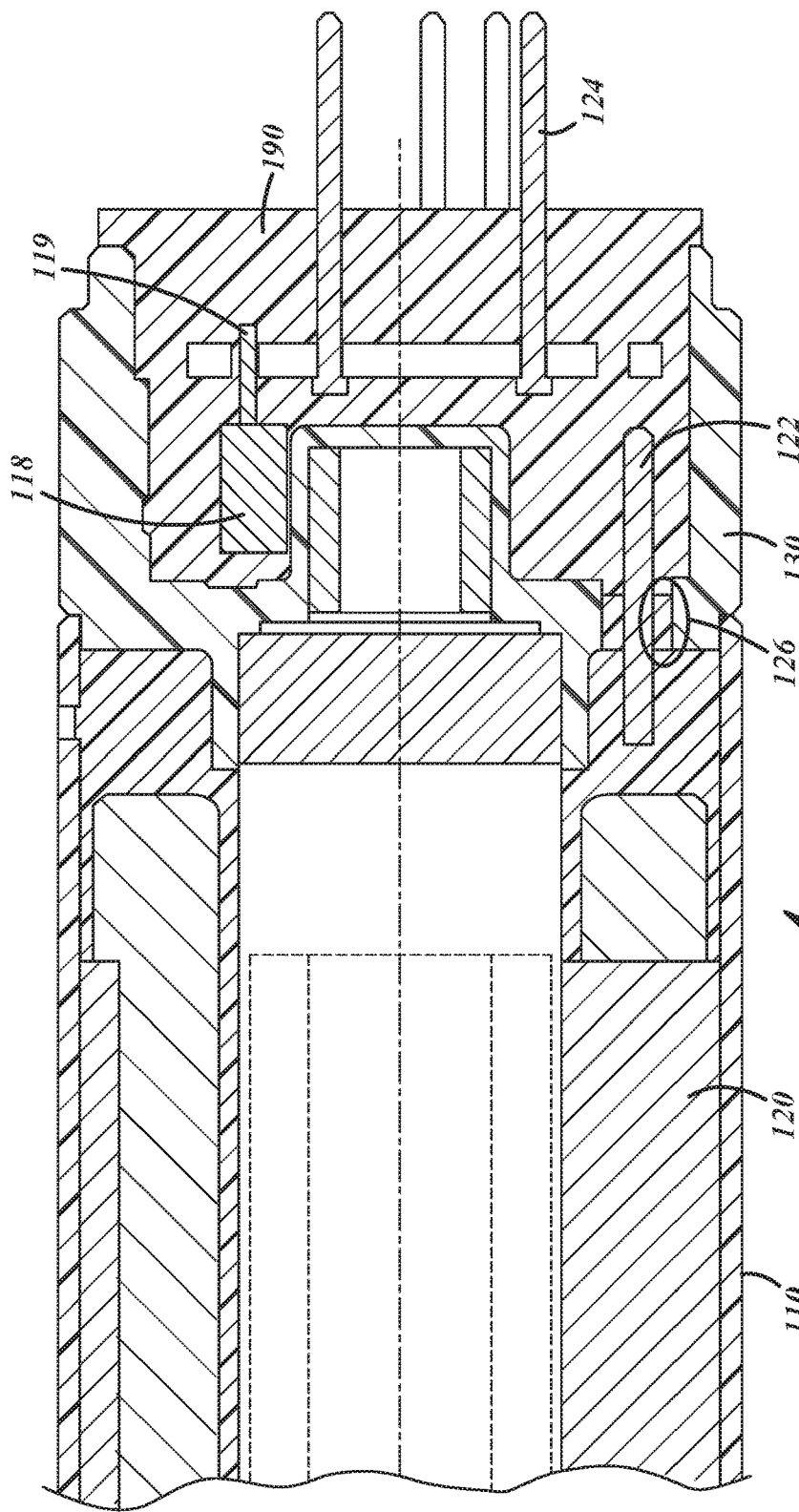
FIG. 3 is a cross-section of details of the example motor configuration of FIG. 2.

FIGS. 2 and 3 are cross-sections of an example motor assembly 100 according to an aspect of the disclosure. The motor assembly 100 includes primary components of a generally cylindrical motor housing 110 with an integrated front endbell 113. A stator assembly 120 is secured within the housing 110 in a manner which will be described below. A rear bearing 116 and commutation magnets 112 are disposed within the housing in cooperative relationship with a rear endbell 130. Rear endbell 130 defines a control module cavity 132, which houses a PCB 180, as well as sensors 118 (one shown in FIG. 2), sensor leads 119 connecting sensors 118, which may be Hall effect sensors, to PCB 180, and external leads 124. At least one PCB to stator lead 122 extends from the PCB 180 thru a glass seal 126 situated in a front wall of the endbell 130 and further to elements of the stator assembly 120. The control module cavity 132 is filled with an encapsulation material 190, which seals and secures the components housed therewithin.

FIG. 4 is an exploded view showing the general assembly of the primary components of an example motor assembly 100 according to an aspect of the disclosure. Housing 110 contains an encapsulation 115, which surrounds a stator frame 121 for supporting stator elements 120. A rotor 150 is secured within front bearing 114 and rear bearing 116 secured within the motor assembly. Rear endbell 130 is secured to an end of the housing 110 and includes encapsulation 190 within the control module cavity of endbell 130.

FIGS. 5 and 6 are perspective views illustrating details of an example rear endbell 130 according to an aspect of the disclosure. The endbell 130 may have a unitary construction and be machined from a single piece of stainless steel, for example. Endbell 130 may include an outer wall 133 and a front wall 134 which defines a control module cavity 132 on a rear side thereof. According to an aspect of the disclosure, front wall is solid, except for stator lead passages 136. Stator lead passage 136 receive stator leads, which are sealed, as will be later explained. Thus, the control module cavity 132 remains isolated from the front of the motor, including areas that may be prone to ingress of contaminating liquids. A rotor end cap 138 may be formed/machined integrally in the front wall 134 for receiving an end of the rotor and housing commutation magnets, as well as permitting advantageous orientation of sensors within the control module cavity, as will be explained.

Referring to FIG. 6, outer wall 133 may include a recessed or thinned portion 139 in relation to the stator lead passages 136, which may be oriented in a circumferential pattern near the perimeter of front wall 134. The recessed or thinned portion 139 of the outer wall 133 is advantageous in permitting location of the stator leads in a manner that maximizes the available space within the control module cavity 132 for other components. More particularly, the orientation and spacing of the stator leads is optimized to provide mechanical and electrical clearance inside the end bell encapsulation, as well as to mitigate electronic interference with other components. These features also provide advantages in assembly of the motor and for improved sealing and encapsulation of the stator leads within the control module cavity.

Endbell 130 may also include an integral forward annular wall which provides a bearing housing 140, which, in combination with the rotor receiving end cap 138 provides for very accurate relative orientation of the commutation magnets and sensors with respect to the rotor and rotor end. Endbell 130 may also include a forward annular housing engaging shoulder 142 for flush mounting of the endbell 130 on housing 110 (FIG. 4). Endbell 130 may be fastened and sealed to the housing by laser welding or other suitable fastening techniques. The rear end of the endbell 130 may include a rear annular shoulder 144 to center endbell 130 to housing 110. An interior circumferential slot 146 provides additional sealing of the encapsulation and secures the encapsulation against axial movement within the control module cavity 132.

FIG. 7 is a perspective view of an example encapsulation 190 (with endbell omitted) according to an aspect of the disclosure. As will be recognized, the recessed or thinned portion of the endbell annular wall (139 in FIGS. 5 and 6) results in an extended portion 192 of the encapsulation 190 in which the stator leads 122 are advantageously sealed, secured and oriented near the perimeter of the encapsulation. Seals 126, which may be glass seals, and which are disposed in the stator lead passages (not shown in FIG. 7) further isolate the portions of the stator leads that extend beyond the endbell front wall to the stator elements. With this configuration, the stator leads are completely isolated from the areas of the motor which are prone to contamination by ingress of liquid. Encapsulation 190 may include a retaining ridge 194 formed during encapsulation as encapsulation material flows into the interior circumferential slot 146 (FIG. 4).

FIG. 8 is a cross-section illustrating an example rear endbell with encapsulation of components in the control module cavity. PCB 180 may be provided with ports 182 for permitting encapsulation material to flow therethrough during a encapsulation process, further securing the PCB 180 in position. Again, as can be seen in this illustration, the PCB 180 and the components thereon, including the sensors 118 may be precisely located relative to the integral rotor end cap 138, and therefore the rotor shaft during an encapsulation step. More particularly, the components may be precisely located on the PCB during a PCB manufacturing step. Then, during motor assembly, the orientation of the PCB and components thereon, including sensors 118 may be precisely controlled by the positioning of the stator leads within the seals and stator lead passages 136. This includes tuning the endbell 130 to housing 110 before encapsulation. This may position the Hall sensors precisely with regard to the stator before encapsulation.

Figure 9:
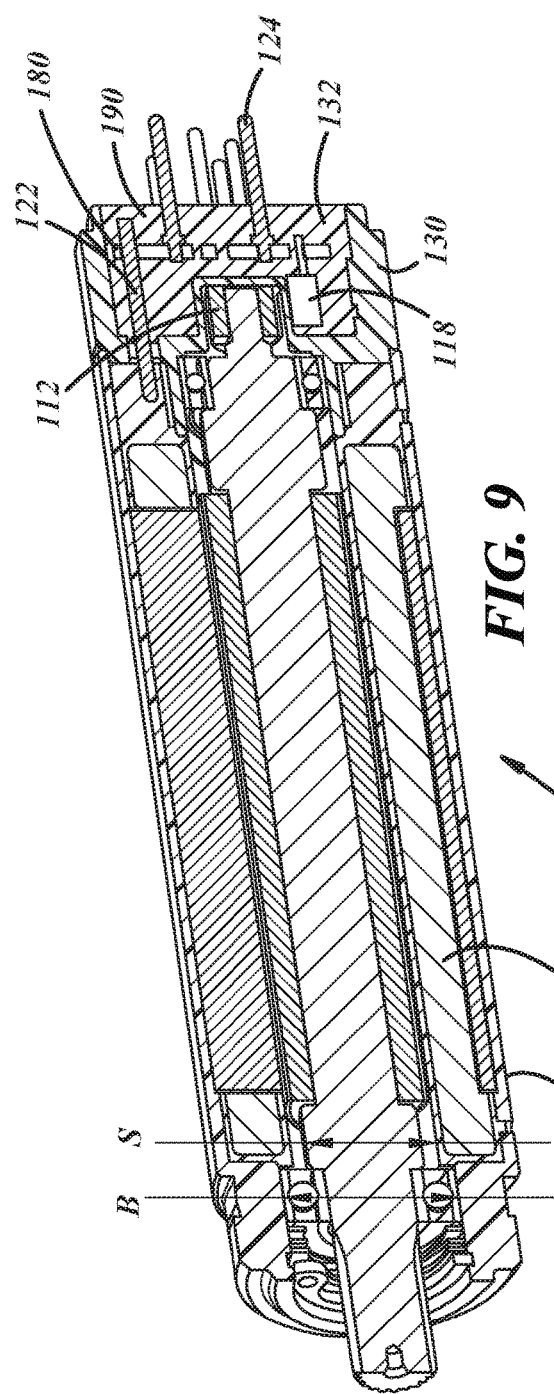
FIG. 9 is a cross-section of an example assembled motor according to an aspect of the disclosure.

FIG. 9 is a cross-section of an example assembled motor according to an aspect of the disclosure.

According to another aspect of the disclosure, the stator elements may be encapsulated into the housing. The encapsulated stator inner diameter—"S" in FIG. 9—is advantageously encapsulated smaller than the diameter of the bearing pocket provided in the front of the housing 110—"B" in FIG. 9. This allows an encapsulation tool, such as a core pin, to create a blind opening, and creating hermetic isolation of Hall magnets (in the front partition of the motor) from the sensors 118, i.e., Hall sensors (in the back partition of the motor). Another advantage is that the larger pocket for the front bearing permits a larger, more durable bearing to be used. In addition, a fixture may be used as part of the encapsulation tooling, to critically align the stator, housing and rear endbell. Such alignment is necessary for precise control and shut-off of the encapsulation material during encapsulation. The fixture may align the core pin with respect to the bearing bore in the endbell. The fixture aligns the front bearing bore of the housing. Finally, the fixture minimizes the potential for runout (affects high speed performance) between the two bearing bores and permits the use of a smaller nominal gap between the stator and the rotor because of the precise alignment provided by the fixture positioning and reduction in the number of components in the tolerance stack-up.

Figure 10:
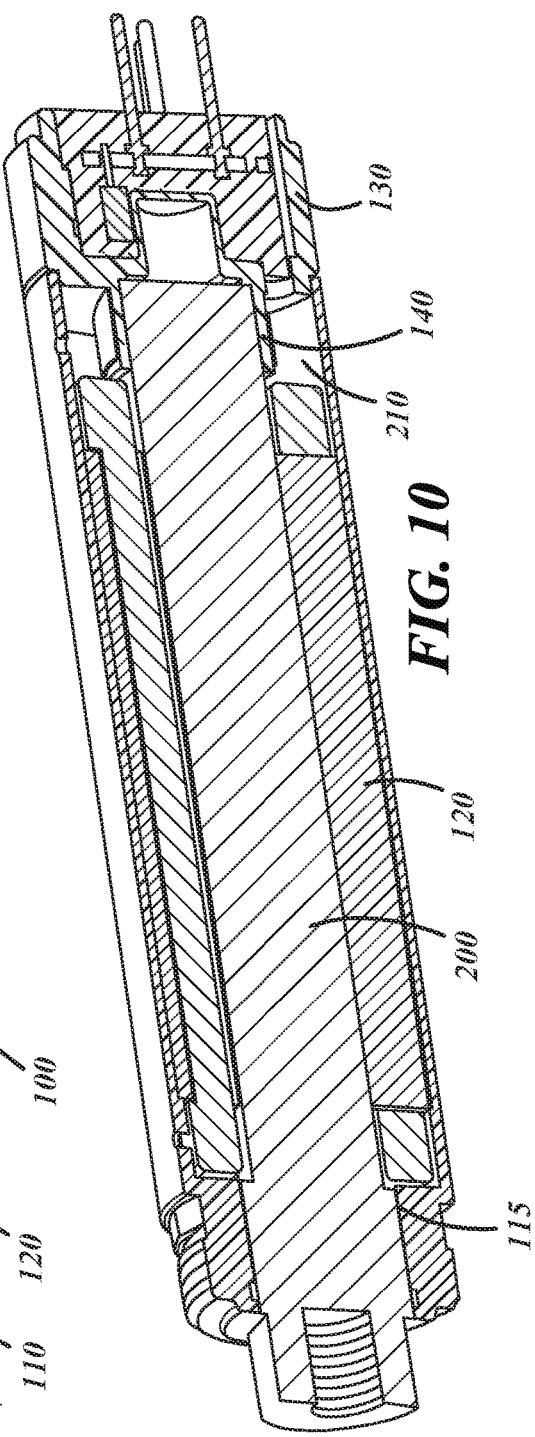
FIG. 10 is a cross-section of an example alignment pin used in a motor assembly process according to an aspect of the disclosure.

According to an example process for motor assembly, the following steps may be undertaken. First, pins 122 (FIG. 8) may be sealed in glass seals within the stator lead passages 136 (FIG. 8) in the endbell 130. Next, the PCB with hall sensors thereon may be assembled over the pins 122 and soldered and bonded in place. This assembly is then encapsulated within the endbell control module cavity. The stator leads are then soldered to the glass pins on the opposite side and the endbell is assembled to the housing 110. Referring to FIG. 10, a first fixture in the form of an alignment pin 200 may be used to align the housing, rear endbell and stator assembly. The alignment pin 200 may have a first end that fits within the rear endbell bearing bore 140 and also has portions that engage the interior diameter of the stator 120 and the housing bearing bore 115 such that these components are held in precise alignment. The motor may be tuned by rotation of the endbell 130 relative to the housing such that the sensors are in a correct orientation to properly control current in the stator elements. Once proper alignment of the rear endbell bearing bore 140, stator interior diameter, and housing bearing bore 115 is achieved, the endbell 130 is fastened to the housing by welding or other fastening techniques. The stator is also fastened in place by bonding to the housing interior using adhesive or other bonding material. A motor-side encapsulation space 210 may be defined in front of the rear endbell 130. Referring additionally to FIG. 11, assembly may also include an encapsulation step to encapsulate the motor side of the rear end bell as well as other internal areas of the motor that require sealing. A pin 300 may be inserted into the housing/stator/endbell assembly and may isolate the housing and rear endbell bearing bores, as well as the stator inside diameter, from encapsulant. Encapsulant may be introduced via one or more ports defined in the housing wall and may flow into encapsulation space 210, further sealing and isolating the components, namely the stator leads and any contaminant migration paths, on the motor side of the rear endbell 130. Following the encapsulation step, the pin 300 may be removed and the motor bearings, rotor and seals installed. As will be recognized, that aforedescribed process provides improved encapsulation and sealing of the components within and adjacent the rear end bell and isolates the control components from contaminants It should be understood that implementation of other variations and modifications of the invention in its various aspects may be readily apparent to those of ordinary skill in the art, and that the invention is not limited by the specific embodiments described herein. It is therefore contemplated to cover, by the present invention any and all modifications, variations or equivalents.

The invention claimed is:

1. A contaminant-resistant motor for surgical applications comprising:
   a housing including a housing wall defining a housing interior;
   a front endbell;
   a rear endbell, having a first side facing the housing interior and a second side, opposite the first side, defining a control module cavity;
   a stator;
   a rotor;
   a control module within the control module cavity of the rear end bell, wherein the control module is hermetically sealed within the control module cavity and isolated from the housing interior.

2. The motor of claim 1, further comprising at least one stator lead extending through a stator lead passage in the rear endbell from the control module in the control module cavity on the second side of the rear endbell to the first side of the rear endbell, the at least one stator lead being sealed against contaminants at least partially by encapsulation within the control module cavity.

3. The motor of claim 2, wherein the at least one stator lead includes a stator lead having an exterior section that extends outside of the control module cavity through the rear endbell to the first side of the rear endbell and wherein the stator lead exterior section extends through a seal disposed in the rear endbell between the first and second sides of the rear endbell for sealing the stator lead exterior section from contaminants.

4. The motor of claim 3, wherein the seal is a glass seal.

5. The motor of claim 1, wherein the control module is hermetically sealed by a first encapsulation in the control module cavity.

6. The motor of claim 5, further comprising at least one sensor in electrical communication with the control module, the at least one sensor being hermetically sealed by the first encapsulation in the control module cavity with the control module.

7. The motor of claim 5, wherein the stator is encapsulated to an interior surface of the housing cavity by a second encapsulation that is separate from the first encapsulation.

8. The motor of claim 7, further comprising a stator lead extending through a stator lead passage in the rear endbell from the control module in the control module cavity on the second side of the rear endbell to the first side of the rear endbell, a first end of the stator lead encapsulated by the first encapsulation, a second end of the stator lead encapsulated by the second encapsulation and the stator lead passing through a seal in the stator lead passage in the rear endbell between the first and second encapsulations.

9. The motor of claim 1, further comprising a bearing pocket formed in a front portion of the housing, wherein an encapsulation of the stator has an inner diameter that is smaller than the diameter of the bearing pocket.

10. The motor of claim 1, further comprising at least one Hall magnet on a motor shaft supporting the rotor that is disposed on the first side of the rear endbell and hermetically isolated from the control module cavity.

11. The motor of claim 1, further comprising a rear bearing disposed within the rear endbell on the first side of the rear endbell, and at least one motor rotation sensor located rearward of the rear bearing on the second side of the rear endbell in the control module cavity.

12. The motor of claim 1, wherein the rear endbell has an exterior surface that is continuous with an exterior surface of the housing.

13. The motor of claim 1, wherein the rear endbell includes a shoulder formed therein for engaging a wall of the housing.

14. The motor of claim 1 wherein the rear endbell defines a rotor end cap on the first side of the rear endbell having a first diameter and configured to receive one end of the rotor and a magnet on a motor shaft supporting the rotor and defines a bearing housing on the first side of the rear endbell forward of the rotor end cap having a second diameter greater than the first diameter and configured to receive a rear bearing supporting the rotor for rotation within the housing.

15. The motor of claim 1 wherein an outer wall of the rear endbell defines an arcuate recessed portion on the second side of the rear endbell axially aligned with a stator lead passage in the rear endbell and configured to receive a stator lead that extends from the control module through the stator lead passage in the rear endbell.

16. A method of making a motor for a surgical device comprising:
providing a motor housing having a housing wall defining a housing interior and an integrally formed front end bell;
arranging a stator within the housing interior;
securing a rear endbell to the housing, the rear endbell having a first side facing the housing interior and a second side, opposite the first side, defining a control module cavity in which a control module is hermetically sealed and isolated from the housing interior; and
placing a rotor within the stator.

17. The method of claim 16, further comprising the step of encapsulating the control module within the control module cavity on the second side of the rear endbell.

18. The method of claim 16, further comprising the step of rotating the rear endbell relative to the housing to orient sensors within the control module cavity relative to the stator.

19. The method of claim 16, further comprising the step of positioning a rear bearing within the rear endbell on the first side of the rear endbell and providing sensors in a location that is rearward of the rear bearing on the second side of the rear endbell in the control module cavity.

20. The method of claim 16, further comprising the steps of aligning a fixture within the housing to align the stator, housing and rear endbell, and encapsulating the stator within the housing.

* * * * *